United States Patent [19]

Trine et al.

[11] 4,102,201
[45] Jul. 25, 1978

[54] VAPOR SAMPLING AND ANALYTICAL DEVICE

[75] Inventors: John A. Trine, Landfall; David L. Braun, Lake Elmo, both of Minn.

[73] Assignee: Minnesota Mining and Manufacturing Company, St. Paul, Minn.

[21] Appl. No.: 836,760

[22] Filed: Sep. 26, 1977

[51] Int. Cl.² .............................................. G01N 1/22
[52] U.S. Cl. ............................. 73/421.5 R; 23/254 R; 55/74; 55/287
[58] Field of Search .................. 73/421.5 R, 23 R; 23/254 R; 55/387

[56] References Cited

U.S. PATENT DOCUMENTS

| 3,681,027 | 8/1972  | Smith ............................... 23/254 R |
| 3,686,835 | 8/1972  | Strange et al. ....................... 73/421.5 |
| 3,985,017 | 10/1976 | Goldsmith ........................ 23/254 R |
| 3,992,153 | 11/1976 | Ferber et al. ....................... 23/254 R |
| 4,046,014 | 9/1977  | Boehringer et al. ............ 73/421.5 R |

Primary Examiner—S. Clement Swisher
Attorney, Agent, or Firm—Cruzan Alexander; Donald M. Sell; Carolyn A. Bates

[57] ABSTRACT

A device and method for collecting selected components of a fluid mixture such as ambient air are disclosed. A chamber formed by wall members and having an open end contains a layer of collecting material on the bottom thereof and a porous layer covering the open end. After this device has been exposed to the fluid mixture for the prescribed time, a solid cap is placed over the open end of the chamber which facilitates introduction and removal of a elutant for subsequent analysis.

17 Claims, 14 Drawing Figures

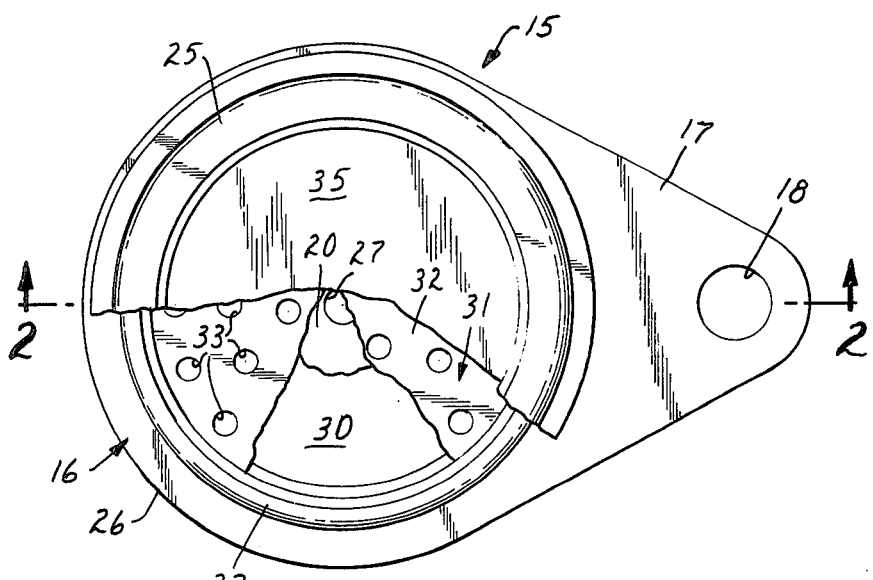
FIG. 1
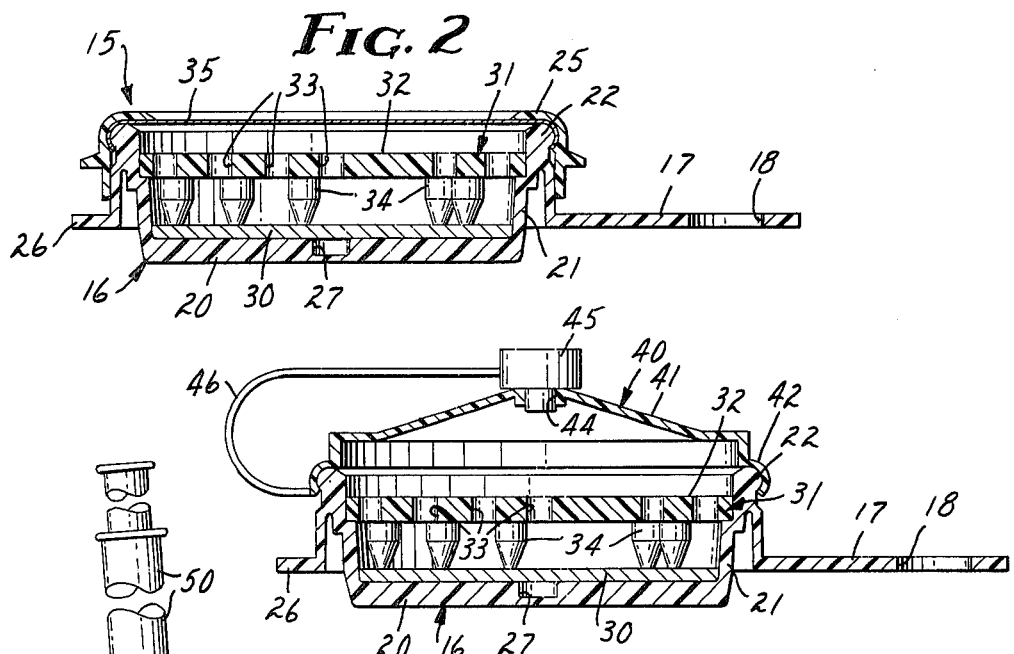
FIG. 2
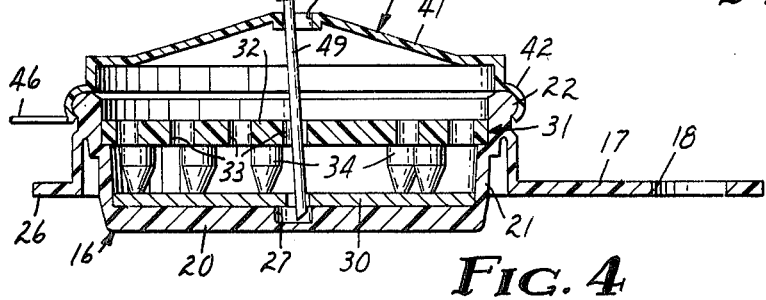
FIG. 3
FIG. 4

VAPOR SAMPLING AND ANALYTICAL DEVICE

The analysis of organic vapors and other gases and vapors in the industrial atmosphere to determine the degree of exposure to workers is now required by law. The method recommended by Occupational Safety and Health Administration (OSHA) to accomplish organic vapor monitoring comprises the following steps: (1) collection of organic vapors on an adsorbent; (2) desorption of the sample from the adsorbent; (3) analysis of the sample collected by gas chromatography; and (4) quantitation of the organic vapors collected.

A typical method of collecting solvent vapors utilizes charcoal tubes of the type described in Bulletin 769, "Determination of Organic Vapors in the Industrial Atmosphere," Supelco, Inc., Bellefonte, Pa. The tubes are made of glass and contain activated coconut shell charcoal as the adsorbent for the organic vapors. Ambient air in close proximity to the breathing zone of the person monitored is pumped through the charcoal tube during the sampling period. When the sample has been collected, the ends of the charcoal tube are capped and the sample is transferred to a laboratory for analysis.

Removal of the collected sample from the charcoal is accomplished by desorption with carbon disulfide ($CS_2$) or some other elutant. This requires breaking of the glass tube, removing the carbon and placing it in a separate vial, and sealing the vial. The elutant ($CS_2$) is then added to the sealed vial, preferably with a syringe. After agitation, an aliquot of the sample is removed and injected into a chromatograph.

This conventional technique suffers from several disadvantages. In transferring the collecting material to a separate vial, the collecting material is exposed to air, and some of the collecting material may be lost or contaminated, thereby introducing errors into the analysis. Furthermore, if the sampling device is made of glass, e.g. a glass tube, which must be broken to accomplish the transfer, there exists the possibility of physical injury to the technician.

An improvement in the general technique, specifically adapted to monitoring exposure to nitrogen dioxide gas, is suggested by Schnakenberg in Technical Progress Report 95, Bureau of Mines, Coal Mine Health and Safety Department, U.S. Department of the Interior, April, 1976 entitled "A Passive Personal Sampler for Nitrogen Dioxide." The sampler comprises an acrylic tube containing three stainless steel screens coated with triethanolamine at one end thereof held in by a polypropylene caplug. The opposite end of the tube has a similar caplug which is removed during the sampling period. At the end of the sampling period, a reagent is added to the tube, the sampler is shaken, and the absorptance of the resulting pink solution is read with a spectrophotometer.

Although this device and technique eliminate the step of transferring the collecting material to a separate vial for desorption of the sample and subsequent analysis, the device doesn't provide a convenient means for introducing and withdrawing the elutant to minimize contamination or evaporative losses of the sample.

SUMMARY OF THE INVENTION

The device of the present invention overcomes many of the deficiencies associated with prior art sampling methods. It utilizes the efficient sampling devices described in U.S. Pat. Nos. 3,924,219 and 3,950,980 in combination with analytical preparatory means adapted for use therewith. This combination allows collection of the sample on, and desorption of the sample from, the collecting medium to be accomplished in the same chamber. The invention eliminates the necessity of transferring the collecting medium to a separate vial for the desorption step, thereby reducing contamination of the sample, increasing accuracy and improving efficiency.

According to the present invention there is provided a device for sampling and analyzing the amount of selected components of a fluid mixture comprising a body having wall members defining a shallow chamber and having an open end. A collecting layer is disposed within the shallow chamber for collecting the selected components. At least one porous layer is supported by the wall members adjacent to the open end and covers the open end for attenuating the flow of the selected components into the chamber. A nonporous cap adapted for engagement with the wall members is provided to seal the chamber after the selected components have been collected. Means are provided in either the nonporous cap or the wall members for introducing into, and removing from the chamber, a liquid elutant for desorbing the selected component from the collecting layer.

When the sampling period is completed, the porous, attenuating layer or layers may be removed (depending on their structure and position with respect to the wall members), and the nonporous or "analyzing" cap is placed over the open end of the device in sealing engagement with the wall members to prevent further contact of the collecting layer with the ambient environment. A liquid elutant is then added to desorb the selected component from the collecting layer. The liquid elutant is conveniently added and subsequently withdrawn through means provided in the analyzing cap or in the wall members. The aliquot withdrawn from the chamber is analyzed in the conventional manner.

The device is especially suited for sampling and analyzing organic vapors in industrial environments. Activated charcoal, alumina, silica gel, and various chromatographic solids are commonly used as the collecting layer, and the organic vapors collected can be conveniently desorbed with carbon disulfide or other liquid elutant. However, the device can be used to sample and analyze any selected component of a fluid mixture which can be collected by a collecting medium and subsequently desorbed therefrom by a liquid elutant.

Significant improvements in convenience and overall accuracy of measurements have been observed with the present invention over prior art devices wherein it was necessary to transfer the collecting material to a glass vial prior to desorption by the elutant.

DESCRIPTION OF THE DRAWINGS

Understanding of the invention will be facilitated by reference to the following drawings wherein:

FIG. 1 is a top plan view partially in section of a sampling device shown ready for use;

FIG. 2 is a cross-sectional view taken along line 2—2 of FIG. 1;

FIG. 3 is a cross-sectional view of the device of FIG. 1 showing one embodiment of the analyzing cap placed on the device;

FIG. 4 is a cross-sectional view of the device illustrating the addition of elutant to the device of FIG. 3;

DETAILED DESCRIPTION OF THE INVENTION

Figure 5:
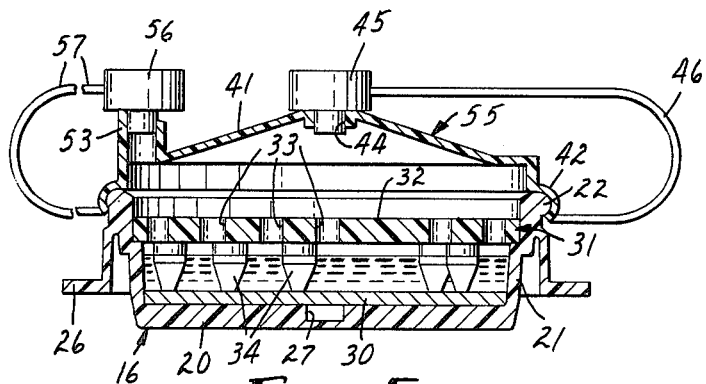
FIG. 5 is a cross-sectional view of the device showing a second embodiment of the analyzing cap.

The sampling device of the present invention is adapted for use in analyzing the amount of a selected component in a fluid mixture. It is adapted to be worn by an individual or positioned in the environment where the selected components are being sampled.

The device is generally illustrated in FIGS. 1 and 2 and designated by the reference numeral 15. It comprises a body 16 which is generally circular in plan view and has a flange 17, extending from the circular body, formed with an opening 18 permitting the device to be suitably fastened in a selected position. The body has wall members defining a shallow chamber which has a circular open end. The wall members comprise a base wall 20 and projecting circular side walls 21. The side walls 21 terminate at their free edges in a rim 22 which has a smooth radius outer lip affording a seal between the body 16 and a membrane retaining ring 25 or to seal thereabouts an analyzing cap according to one of the embodiments thereof to be hereinafter described. Depending from the rim 22 of the wall members 21 and extending thereabouts are outer circular walls 26 which protect the side walls of the chamber and which are formed with an outwardly extending flange which is disposed in the same plan as the flange 17. The base wall 20 is provided with a centrally disposed shallow recess 27 opening into the chamber.

Disposed within the shallow chamber formed by the wall members are a collecting layer 30 disposed adjacent to base wall 20, a foraminous attenuating member 31 which comprises a circular plate 32 having tiny channels 33 and which is supported from the detecting layer by a plurality of posts 34. Also, there is disposed about the rim 22 and retained by the ring 25 a microporous membrane 35 forming a further attenuating layer for the fluid being sampled. The large central opening of the ring 25 exposes a large area of the membrane 35.

The collecting layer 30 may comprise any material which absorbs, adsorbs, reacts with or otherwise collects the selected component being sampled. An example of a suitable detecting layer for sampling organic vapors is activated charcoal or other particulate sorbent held in a matrix formed by polytetrafluoroethylene as described in copending application Ser. No. 836,763 filed Sept. 26, 1977 assigned to the assignee of the present application.

After the device 15 illustrated in FIGS. 1 and 2 has been exposed for a predetermined interval to the fluid being sampled for the selected component, the retaining ring 25 and the attenuating layer 35 are removed from the rim 22 of the body 16, and the analyzing cap is placed thereon to permit an elutant to be retained within the shallow chamber to desorb the selected component from the collecting layer. The analyzing cap permits the sampling and the desorbing steps to take place within the monitoring device. This avoids contamination and decreased accuracy which may result from the removal of the collecting layer from the monitoring device and placing the same in an external vial for the purpose of desorbing the selected component. Efficiency of the analyzing procedure is also greatly enhanced.

One embodiment of the analyzing cap is disclosed in FIG. 3 and generally designated by the reference numeral 40. This cap comprises a generally circular domed-shaped cover plate 41 with a surrounding flange 42 which mates with the sealing lip of the rim 22 of the body 16. The analyzing cap is formed with an opening 44 and a plug 45 which will frictionally seal the opening. The plug 45 is secured by flexible band 46 to the flange of the cap to avoid loss during displacement of the plug 45 from the opening 44.

Referring now to FIG. 4, after the analyzing cap has been placed over the body member 16, the plug 45 of FIG. 3 can be removed from the sealing position in the opening 44 and a needle 49 attached to a syringe 50 may be positioned through the opening 44. The needle 49 is then directed through channel 33 in the plate 32 and through the collecting layer 30 or a corresponding hole in the collecting layer 30 into the recess 27 to discharge into the shallow chamber a liquid elutant for desorbing the selected component from the collecting layer or to withdraw an aliquot of the sample therefrom.

Figure 6:
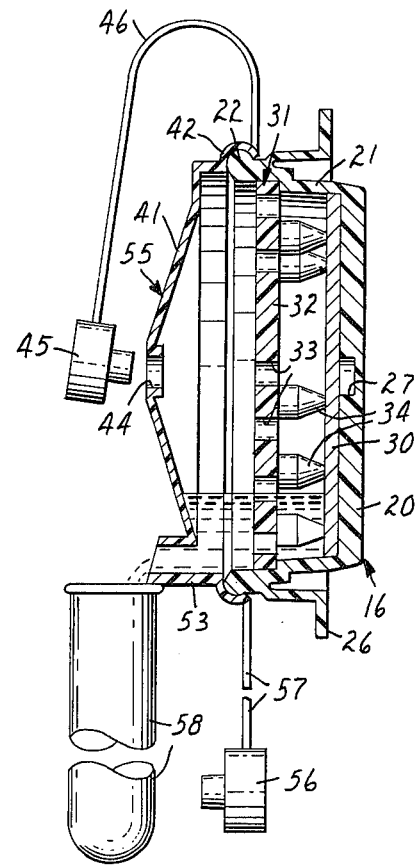
FIG. 6 is a cross-sectional view illustrating decanting of the elutant from the device of FIG. 5.

Referring now to FIG. 5, a second embodiment of an analyzing cap 55 is disclosed which is generally similar to the analyzing cap 40 of FIG. 3 having a domed cover plate 41 and a generally circular flange 42 which seals with the lip on the rim 22 of the body member 16. The cap 55 differs from the cap 40 of FIG. 3 by having a spout positioned adjacent the edge of the cap. The spout is formed by a short cylindrical wall member 53 defining a cylindrical passageway from the interior of the circular cover to an external circular opening. This opening is provided with a plug 56 which is attached to the cover 55 by a band 57. The spout formed by the cylindrical wall 53 permits the elutant to be decanted from the body of the sampling device as illustrated in FIG. 6 upon removal of the plug 56 and tipping the body member to position the spout on the lower side thereof allowing the aliquot to drain into a receptacle such as a test tube 58.

Figure 7:
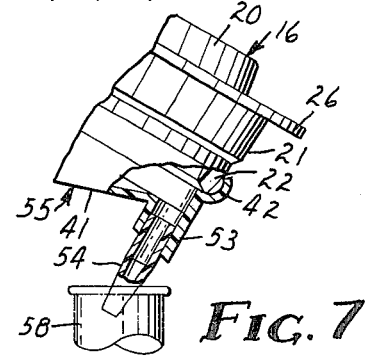
FIG. 7 is a partial sectional view of the device of FIG. 6 showing an alternative decanting means.

In FIG. 7 a nozzle-like attachment 54 to the pouring spout is illustrated. Attachment 54 frictionally fits into the pour spout to extend the length thereof. The tip of attachment 54 may be positioned inside the mouth of the receptacle 58 so that no liquid is spilled during decantation. Attachment 54 is especially useful when elutants having low surface tension are decanted.

Figure 8:
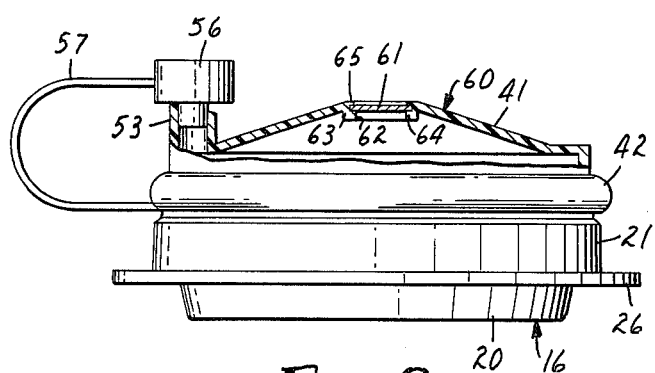
FIG. 8 is a partial sectional view of the device showing a third embodiment of the analyzing cap.
Figure 9:
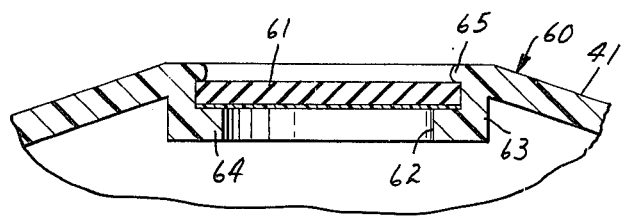
FIG. 9 is an enlarged detail sectional view of the top center portion of the analyzing cap of the device of FIG. 8.

FIG. 8 illustrates a third embodiment of the analyzing cap generally designated 60. This cap is again similar to previous caps 40 of FIG. 3 and 55 of FIG. 5, however the opening 44 and plug 45 have been removed from the central portion of the cover plate 41 and the opening is formed to receive and captively retain a septum 61. The modified opening in the analyzing cap 60 is shown in detail in FIG. 9 wherein there is illustrated an opening 62 defined by a flange 63 which is provided with a shoulder 64 which supports the septum 61. The septum is positioned between the shoulder 64 and an opposed lip 65 which captively retains the septum in place over the opening 62. The septum 61 is formed of a disc shaped piece of a flexible, resilient, inert and self-sealing material such as silicone rubber which may be penetrated by a needle to permit the elutant to be deposited in the chamber of the analyzing device. When the septum is penetrated and the elutant injected into the chamber, plug 56 should be removed from the spout 53 to allow pressure within the chamber to equalize. Following desorption of the selected component from the collecting layer, the elutant may be removed through the septum 61 with a needle and syringe, or alternatively the elutant may be decanted through the pour spout provided the septum is vented by insertion of a needle for passage of a volume of air equal to the volume of liquid decanted.

Figure 10:
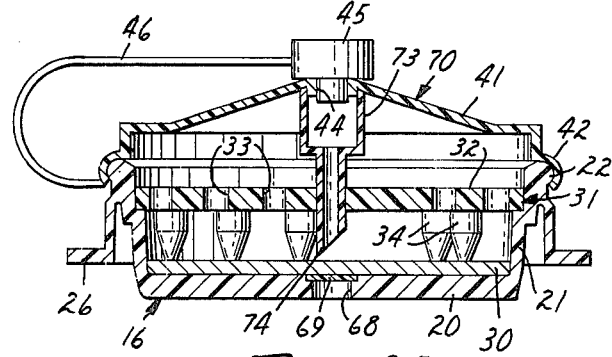
FIG. 10 is a cross-sectional view of the device showing a fourth embodiment of the analyzing cap and a second embodiment of sampling device.

In FIG. 10 the analyzing device is again modified to show an alternative embodiment. In this device the base wall 20 of the body 16 is formed with an opening 68 which extends therethrough rather than having the recess 27 of FIG. 4. Positioned in the opening and seated against shoulders formed therein is a membrane 69 or thin section of polymer integrally molded thereto which normally closes opening 68. The cap 70 is formed with a central opening corresponding to the opening 44 and it is normally sealed by plug 45. Formed integrally with the cap and positioned on the interior surface thereof is a needle-like structure 73 which is a generally cylindrical structure terminating at its lower end in a bevelled edge to form a sharpened end 74. After the elutant has been injected into the chamber through the hole in the cap by removing the plug 45, the plug is replaced and the elutant is allowed to desorb the selected component from the collecting layer. The elutant is then extracted from the body member by applying sufficient force against the plug 45 that the cover plate 41 flexes sufficiently to allow the point 74 of the needle-like structure 73 to puncture the membrane 69 forming an opening therein through which the elutant may be extracted through the opening 68 in the base wall of the body member. The pour spout of FIG. 6 may be used to facilitate transfer of the elutant for analysis.

Figure 11:
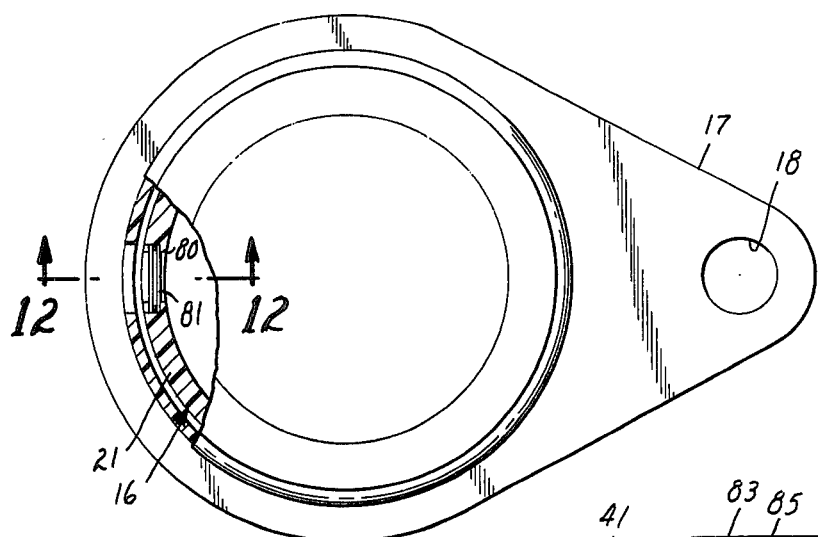
FIG. 11 is a top plan view, partially in section of a further embodiment of the sampling device constructed according to the present invention.
Figure 12:
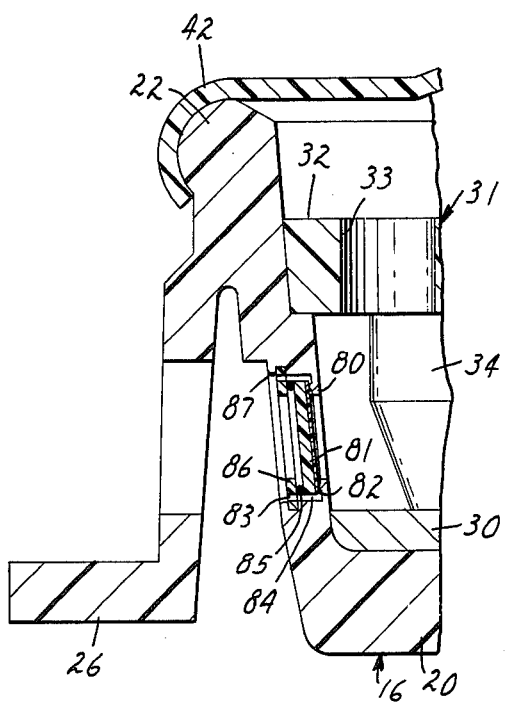
FIG. 12 is an enlarged detail sectional view of the device of FIG. 11 taken along line 12—12.

In FIG. 11 there is illustrated a modification of the body 16. In this embodiment the side wall 21 of the body member is formed with an opening which is provided with a self closing and penetrative septum and a structure which is self venting about the margin of the septum as the gas pressure within the chamber formed by the body member and the analyzing cap exceeds a predetermined pressure. As illustrated in FIG. 12 this opening is generally circular and is defined by a flange 80 extending into the opening on the interior side of the side wall 21 which forms a shoulder to support the septum 81. The shoulder is provided with a circular rib 82 which forms the seal with the septum 81. The opening is generally circular, but is provided with axially extending passageways 84 spaced about the periphery thereof to form relief passageways for the gas after it has displaced the septum 81 from its sealing engagement with the rib 82. The septum 81 is normally retained in a sealing position by an O-ring 85 which is positioned within the opening and retained against the septum 81 by captively held ring 86 positioned in the opening and retained by lips 87 formed on the exterior side of the side wall 21. The ring 86 is provided with tiny openings 83 which align with the passageways 84 positioned about the opening to permit the gas to escape from the body member through a passageway 84 and the opening in the ring.

A self venting opening such as shown in FIG. 12 can also be placed into the analyzing cap. When positioned in the cap the self venting opening may form the only opening therein thus allowing the elutant to be introduced through the penetrative septum and removed through the septum by the use of the needle and syringe. The structure of the opening and the self venting structure is similar to that described for the side wall of the body member 16 as illustrated in FIG. 12 and the same reference numerals are utilized on the structure as shown in the analyzing cap 90 in FIGS. 13 and 14.

The invention may be further illustrated by reference to the following nonlimiting examples.

EXAMPLE 1

External Analytical Preparation

This example provides a basis of comparison for later examples. In this example the collecting layer is transferred to a separate vial for analytical preparation.

Monitors of FIG. 1 were injection molded using DuPont Zytel 66 nylon resin. The microporous membrane (reference numeral 35) was Celgard ®2400, a microporous polypropylene. Carbon wafers bonded to Teflon porous matrix were prepared according to the methods described in co-pending application Ser. No. 836,763 filed Sept. 26, 1977 assigned to assignee of this application. The wafers we 1.2 inches (3.05 cm) in diameter, 0.020 inches (0.05 cm) thick and consisted of a blend of 60% activated carbon, 20% "Teflon," and 20% kaolin. The wafers weighed about 200 mg each.

Twelve monitors were assembled and were exposed to 121 ppm toluene. Four monitors were removed after three hours and sealed with an analyzing cap of FIG. 3. Similarly, four monitors were removed and capped after five hours. After eight hours the last four monitors were removed and left uncapped. For purposes of this example, the analyzing cap was used only to prevent further exposure of the collecting layer.

All monitors were analyzed 12 hours later by removing each carbon wafer from the monitor to a sealed glass vial and desorbing the toluene at room temperature in 1.0 ml carbon disulfide ($CS_2$) for a minimum of 30 minutes. An aliquot (3 $\mu$l) was injected into an HP-5830A Hewlett-Packard Gas Chromatograph. The data obtained are presented below:

| Exposure to 121 ppm Toluene followed by external analytical preparation | | | |
|---|---|---|---|
| Number of Monitors | Exposure Period (hrs.) | Average Toluene Collected ($\mu$g) | S.D. ($\mu$g) |
| 4 | 3 | 1489 | 45.3 |
| 4 | 5 | 2443 | 46.3 |
| 4 | 8 | 3815 | 89.1 |

The average amount of toluene collected per hour for the three, five, and eight hour periods was 496, 489, and 478 respectively. These values are essentially the same because the smallest standard deviation is more than twice the largest difference between hourly rates.

EXAMPLE 2

Internal Analytical Preparation Using Polypropylene Device

Monitors of FIG. 1 were injection molded from Hercules Profax 6523 polypropylene. A series of activated carbon discs formed by die-cutting 1.2 inch (3.5 cm) pieces from a sheet of 3M Brand Pluton Foundry Cloth were used as collecting layers. The carbon had a surface area of about 600 m²/gram and the discs were 0.5 mm thick and weighed about 160 mg each.

Twelve monitors were assembled and exposed to 375 ppm methyl ethyl ketone (MEK). Monitors were removed from the test after variable time periods and capped with analyzing caps illustrated in FIG. 3. One ml of reagent grade carbon disulfide was directly added to each monitor through the syringe port and the plug was replaced. After an elution period strictly held to 30 minutes, aliquots (3 $\mu$l) were withdrawn and injected into an HP 5830A chromatograph for analysis. Results are shown below:

| | Exposure to 375 ppm MEK Followed by Internal Analytical Preparation | |
|---|---|---|
| Number of Monitors | Exposure Period (hrs.) | Average Micrograms MEK Collected |
| 3 | 1.0 | 528 |
| 3 | 2.0 | 934 |
| 3 | 3.0 | 1551 |
| 3 | 4.0 | 2118 |

The increase in micrograms of MEK collected is found to relate directly to the incremental exposure time periods.

In this example the elution period was held to 30 minutes to preclude variability from permeation of the $CS_2$ into the polypropylene. Such permeation might cause errors. none-the-less, polypropylene and other materials which allow permeation of the elutant are useful so long as the elution time period is fixed and the rate of permeation is taken into account.

EXAMPLE 3

High Precision Internal Analytical Preparation

Monitors of FIG. 1 were prepared as in Example 1 and analyzing caps as shown in FIG. 3 were placed thereon following the exposure period. Standard silicone stopcock grease was used to seal flange 42 of the analyzing cap of FIG. 3 to rim 22 of the body 16. A film of grease of about 0.001 inches (0.0025 cm) thick was used.

Eight monitors were exposed to toluene at about 100 ppm for four hours and then capped. One ml of $CS_2$ was injected directly into the monitor via the syringe port and the plug replaced. The monitor was gently tipped several times through an angle of no more than 5° from horizontal to promote mixing of the elutant and sample. The elutant was analyzed as described in Example 2. The results are shown below:

| Exposure to 100 ppm Toluene Followed by Internal Analytical Preparation | | |
|---|---|---|
| Monitor | Toluene Collected ($\mu$g) | |
| 1 | 1723 | Mean = 1655 |
| 2 | 1659 | S.D. = 42.96 |
| 3 | 1674 | |

| Exposure to 100 ppm Toluene Followed by Internal Analytical Preparation | |
|---|---|
| Monitor | Toluene Collected ($\mu$g) |
| 4 | 1663 |
| 5 | 1647 |
| 6 | 1660 |
| 7 | 1650 |
| 8 | 1567 |

The standard deviation is superior to the best standard deviation found in Example 1 where external analytical preparation was used.

EXAMPLE 4

Direct Comparison of Internal and External Analytical Preparations

Twelve monitors as described in Example 3 were exposed to MEK at about 185 ppm for 7.5 hours. After the exposures, six monitors were analyzed by removing the carbon wafer and transferring it to a separate vial as in Example 1 and six monitors were analyzed by the internal analytical preparation technique as in Example 3. The results were as follows:

| External Preparation Micrograms MEK | Internal Preparation Micrograms MEK |
|---|---|
| 1 - 3529.9 | 1 - 3503.4 |
| 2 - 3567.3 | 2 - 3524.3 |
| 3 - 3693.1 | 3 - 3511.8 |
| 4 - 3593.4 | 4 - 3467.4 |
| 5 - 3650.5 | 5 - 3613.6 |
| 6 - 3553.2 | 6 - 3609.9 |
| Mean = 3597.9 | Mean = 3538.4 |
| S.D. = 62.3 | S.D. = 59.9 |
| Range = 162.2 | Range = 146.2 |

These data indicate that the internal analytical preparation technique results in an essentially equivalent mean value and a slightly superior standard deviation and a lower range.

Three of the monitors where internal analytical preparation was used were analyzed again after several hours. The average number of micrograms found was within 4.0 percent of the original values.

EXAMPLE 5

Internal Analytical Preparation

Organic vapor monitors were constructed as shown in FIGS. 1 and 3. The foraminous attenuating member 31, the body 16, and analyzing cap 40 were injection molded from DuPont Zytel ®66 nylon resin.

A seal between the rim 22 of the body 16 and the retaining ring 25, and between the rim 22 and the flange 42 of the analyzing cap was made by smearing less than 0.001 inch (0.0025 cm) thick of Dow Corning high vacuum grease onto the parts before the parts were joined.

The microporous membrane 35 was Celgard ®2400, a microporous polypropylene sheet 0.001 inch thick. The membrane was held in place by compressing it between the retaining ring 25 and the rim 22 of the body; taking special care to avoid wrinkles on the exposed face of the Celgard ®.

The collecting layer was an activated carbon bed suspended in a polytetrafluoroethylene matrix as disclosed in co-pending application U.S. Ser. No. 836,763 filed Sept. 26, 1977. Each substrate contained 210 ± 20 mg of activated carbon and was about 0.016 inches (0.04 cm) thick and 1.2 inches (3.05 cm) in diameter. A series of organic vapor monitors as described above were exposed to different organic vapors. Following exposure the collected vapors were desorbed from the collecting layer with 1.0 ml $CS_2$, and an aliquot analyzed as in Example 2. The results are tabulated below.

| Exposures to Variety of Organic Vapors Followed by Internal Analytical Preparation | | |
|---|---|---|
| Vapor | Approximate Concentration | $\mu$g/hr ± S.D. |
| MEK | 125 ppm | 415 ± 11.8 |
| Toluene | 100 ppm | 343 ± 8.51 |
| Chlorobenzene | 75 ppm | 267 ± 6.66 |
| Tricloroethylene | 100 ppm | 575 ± 14.3 |
| Ethylbenzene | 100 ppm | 395 ± 5.14 |
| Cyclohexene | 350 ppm | 1226 ± 37.7 |

This example demonstrates the highly precise results that are obtained using internal analytical preparation. The standard deviations range from 1.5 percent to 3.0 percent of the mean. The best precision obtained with external analytical preparation in Example 1 was 46.3 or 1.9 percent of the mean.

EXAMPLE 6

Decanting Option

Analyzing caps as shown in FIG. 5 were made using DuPont Zytel 66 nylon. For testing the decanting pour spout, monitors were made using the device of FIG. 1 and the analyzing caps of FIG. 5. One ml of $cs_2$ elutant was added to the monitor through the syringe port. During the elution period of 30 minutes the plugs in the syringe port and in the decanting pour spout were left in place. After the elution time, the pour spout was opened and the syringe port was opened to allow venting. The mouth of a 1.0 ml glass vial was placed over the pour spout and the monitor was inverted to catch free liquid. About 0.52 ml was collected, the remaining elutant being held in the collecting layer (polytetrafluoroethylene-activated charcoal composite sheet described in Example 1.)

The 0.52 ml collected was ample for use on an HP 7671A Automatic Sampler. It was concluded that the internal sample preparation combined with the decant capability allows one to automatically analyze the elutant without the need for handling the collecting layer or using syringe transfer of elutant from the monitor after elution. Sample contamination is thereby minimized. In addition, long term storage of the sample is provided.

EXAMPLE 7

Bonded Septum Analyzing Cap

The object of this example is to show that the bonded septums can provide access to the sample inside the monitor. In Examples 1 through 6 this access was provided by opening the syringe port.

Five monitors of FIG. 5 were made with the exception that on each of the monitors, a 2 mm hole was drilled on each cap alongside the syringe port to make a monitor functionally equivalent to FIG. 7. Then a silicone rubber septum (Supelco Cat. No. 02-0448) was bonded to the cap over the hole.

Similarly, "Teflon"-faced septums (Supelco Cat. No. 02-0459) were used on five other monitors. Three monitors with no septums were used as controls.

About 7500 micrograms of trichlorethylene was injected into each monitor. After 12 hours, the monitors were analyzed according to the procedure outlined in Example 2. Results were as shown below:

| | Exposure to 7500 Micrograms Trichloroethylene Followed by Internal Analytical Preparation | | | |
|---|---|---|---|---|
| Group | Monitor | Sample Type | Micrograms Trichloroethylene | Mean, S.D. |
| A | 1 | Control | 7875 | 7714, 162 |
|   | 2 | Control | 7716 | |
|   | 3 | Control | 7551 | |
| B | 4 | Silicone | 8451 | 7483, 608 |
|   | 5 | Silicone | 6966 | |
|   | 6 | Silicone | 6998 | |
|   | 7 | Silicone | 7359 | |
|   | 8 | Silicone | 7641 | |
| C | 9 | Silicone/Teflon | 7114 | 7497, 290 |
|   | 10 | Silicone/Teflon | 7379 | |
|   | 11 | Silicone/Teflon | 7658 | |
|   | 12 | Silicone/Teflon | 7452 | |
|   | 13 | Silicone/Teflon | 7882 | |

In these results, the greatest difference between means is the 3.0 percent difference between Group A and Group B which is within acceptable limits. Therefore, it was concluded that septums provide a useful means for access to the sample.

EXAMPLE 8

Auto Venting Septum

Figure 13:
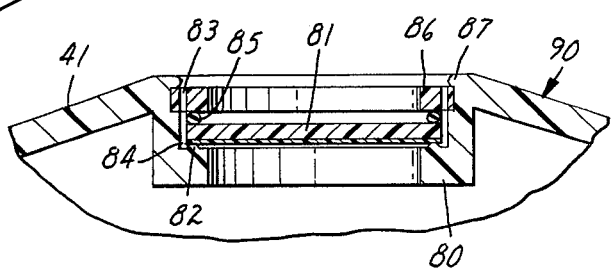
FIG. 13 is an enlarged detail sectional view of a further embodiment of an analyzing cap showing an additional embodiment of the invention.
Figure 14:
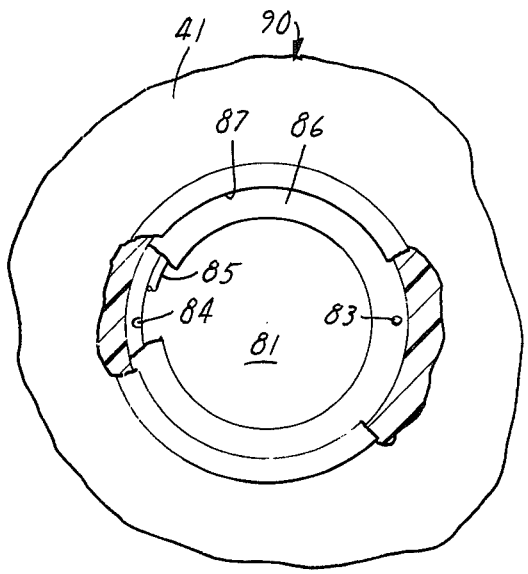
FIG. 14 is a detail plan view partially in sectional of the analyzing cap of FIG. 13.

The auto venting septum arrangement of FIGS. 13 and 14 was fabricated from a machined aluminum rod by drilling out a cavity in the rod. A Hewlett Packard septum (11 mm diameter and 2.5 mm thick) and a compressible ring 0.3125 in. (0.7937 cm) inside diameter by 0.0625 in. (0.1587 cm) thick rubber "O" ring were used. The autoventing septum assembly closed the open end of the aluminum cavity. The captively held ring 86 could be adjusted to vary the amount of compression in the compressible ring and septum.

The auto venting septum should retain a seal when the pressure within the chamber falls below ambient pressure or is equal to ambient pressure. Increases in the pressure within the chamber should be accompanied by a controlled venting so as to equalize the pressure.

To test the performance of the septum, vacuum, or positive pressure were alternately applied to the chamber by inserting the needle (1.5 cm × 0.2 mm) of a 10 cc ground glass TOMAC syringe through the septum. All tests were started at the 6.0 cc position of the syringe. The vacuum test consisted of a retraction of the plunger to the 10.0 cc position followed by release of the plunger and its recovery to an equilibrium position equal to 6.0cc or greater. Positions greater than 6.0 cc indicated that amount of the leak. The readings in the table below under the heading "Vacuum Test" indicate the syringe readings. Thus, test #1 shows a leak of 0.3 $cm^3$ (6.3 − 6.0 = 0.3).

To demonstrate the venting characteristic of the septum, the plunger was forced from the 6.0 cc position to 0.0 cc and held for a measured time period (relaxation time) after which it was allowed to move outward from the 0.0 cc position. Unvented air was indicated by the resulting syringe position. The column headed "Venting Test" indicates the amount of unvented gas. Thus, test #4 shows 1.2 $cm^3$ of fluid unvented.

Axial adjustments of the ring 86 were made to study the effect of compression or relaxation of the septum and the compressible ring. A metric micrometer was used to measure the displacement from an arbitrary zero. The arbitrary zero setting is a point just past the point of initial contact. The starting point for displacement is designated 0.000 and positive (+) displacements indicate compression and negative (−) displacements are indicative of relaxation of compression force.

| Auto Venting Septum Performance Test | | | | |
|---|---|---|---|---|
| Test | Displacement (centimeters) | Vacuum Test (cm$^3$) | Venting Test (cm$^3$) | Time to Relaxation (seconds) |
| 1 | +0.015 | 6.3 | | |
| 2 | +0.015 | 6.2 | | |
| 3 | +0.015 | 6.2 | | |
| 4 | +0.015 | 6.3 | 1.2 | 5 |
| 5 | +0.010 | 6.2 | 0.5 | 5 |
| 6 | +0.010 | 6.2 | 0.3 | 5 |
| 7 | +0.005 | 6.1 | 0.0 | 5 |
| 8 | +0.005 | 6.1 | 0.0 | 5 |
| 9 | −0.000 | 6.1 | 0.0 | 5 |
| 10 | −0.000 | 6.1 | 0.0 | 5 |
| 11 | −0.005 | 6.2 | 0.0 | 3 |
| 12 | −0.005 | 6.3 | 0.0 | 2 |
| 13 | −0.010 | 6.7 | 0.0 | 1 |

Vacuum test results less than or equal to 6.3 cm$^3$ were viewed as an adequate seal because leakage around the ground glass of the syringe results in readings of about 6.1 cm$^3$. Therefore, a 6.1 cm$^3$ reading indicates a complete seal.

Complete venting is demonstrated by a 0.0 reading in the Venting Test indicating no outward motion of the plunger after the indicated time period. In test #4, the 1.2 reading for the Venting Test means that after 5 seconds, 1.2 cm$^3$ of the original 6.0 cm$^3$ remained to be vented.

Tests 5 through 12 demonstrate the range of adequate performance with Tests 7 through 10 showing superior performance wherein venting and sealing are complete.

EXAMPLE 9

In Example 5 the best precision obtained was about 1.5 percent of the mean. By reducing the clearance between the rim 22 and the seal area 42 of the cap 40 of FIG. 3 to a mild interference fit, the need for using the high vacuum grease of Example 5 was eliminated and a precision superior to that obtained in Example 5 was observed.

Monitors of FIGS. 1 through 3 were made as in Example 5 except that the high vacuum grease was eliminated. The seal was provided by reducing the clearance in the cap to body seal area. Four monitors were exposed to benzene vapor at 4.22 ppm for 6 hours and 2 minutes. At the same time three samples were taken using carbon tubes of the type described in Bulletin 769, "Determination of Organic Vapors in the Industrial Atmosphere," Supelco, Inc., Bellefonte, Pa. Results were as follows:

| Carbon Tube Samples with External Preparation ($\mu$g Benzene) | Monitors of FIGS. 1-3 with Internal Preparation ($\mu$g Benzene) |
|---|---|
| 13.3 | 197.0 |
| 13.3 | 195.0 |
| 14.4 | 194.0 |
|  | 192.0 |
| Mean = 13.67 | Mean = 194.5 |
| S.D. = 0.64 | S.D. = 2.08 |

The relative standard deviation of the monitors of the present invention is 1.06 percent of the mean compared with 4.68 percent for the carbon tubes. This shows the superior precision of the internal analytical preparation.

What is claimed is:

1. A device for sampling and analyzing the amount of at least one selected component of a fluid mixture comprising:
    a body having wall members defining a chamber having an open end;
    a collecting layer disposed within said chamber for collecting said selected component;
    at least one porous attenuating layer supported in said chamber adjacent said open end and covering said open end;
    a nonporous cap adapted for engagement with said wall members to seal said chamber at said open end; and
    means in one of said nonporous cap and said wall members for introducing and removing a liquid elutant from said chamber for desorbing said selected component from said detecting layer for analysis.

2. The device according to claim 1 wherein said wall members include a base wall opposite said open end and upstanding side walls.

3. The device according to claim 2 wherein said base wall contains a centrally disposed shallow recess.

4. The device according to claim 1 wherein said collecting layer comprises activated charcoal.

5. The device according to claim 1 wherein said porous attenuating layer comprises a plate having channels therethrough and means spacing said plate from said detecting layer.

6. The device according to claim 1 wherein said porous attenuating layer comprises a microporous membrane.

7. The device according to claim 2 wherein said nonporous cap comprises a cover plate with an opening and a removable plug for introducing and removing a liquid elutant from said chamber.

8. The device according to claim 7 wherein said opening aligns with a recess in said base wall.

9. The device according to claim 7 wherein said nonporous cap contains a pour spout and a removable plug.

10. The device according to claim 1 wherein said nonporous cap comprises a coverplate having a self-sealing septum therein for penetration by a needle for introducing a liquid elutant into said chamber and venting means for relieving pressure within said chamber.

11. The device according to claim 10 wherein said venting means comprises a valve structure including a septum resiliently held over an opening in said cap, said septum being movable to an open position when the pressure within said chamber reaches a predetermined pressure allowing the escape of gas through passageways positioned about the periphery of said septum.

12. The device according to claim 10 wherein said venting means comprises a valve structure including a septum resiliently held, by an elastomeric ring over an annular opening in said cap, said septum being movable to an open position when the pressure within said chamber reaches a predetermined pressure allowing the escape of gas through passageways positioned about the periphery of said septum and extending axially in relationship to said opening.

13. The device according to claim 2 wherein said side walls have a self-sealing septum therein for penetration by a needle for introducing a liquid elutant into said chamber, said chamber having venting means for relieving pressure within said chamber.

14. The device according to claim 7 wherein said wall members include a base wall opposite said open end, said base wall having an opening therethrough which is closed by a thin penetratable membrane, and wherein said cover plate has a generally cylindrical hollow needle-like structure integral therewith and communicating with said opening in said cover plate, said needle-like structure terminating at its distal end with a sharpened end disposed in aligned spaced relationship with said opening in the base wall for puncturing said membrane upon flexure of said cover plate.

15. A method of determining the amount of at least one selected component of a fluid mixture comprising the steps of:
collecting the selected component by exposing said fluid mixture for a measured period of time to a collecting layer disposed within a chamber formed by body members and having an open end with at least one porous attenuating layer disposed across said open end to allow passage of said fluid into said chamber;
sealing said chamber at the expiration of said measured period;
adding to said chamber a measured amount on an elutant to desorb the selected component from said collecting layer;
withdrawing an aliquot of the elutant containing the selected component;
analyzing the solution to determine the amount of the selected component present therein.

16. The method according to claim 15 wherein said chamber is sealed by placing a cap over said open end, said cap having means therein for introducing and withdrawing said elutant.

17. The method according to claim 15 wherein said elutant is added to, and withdrawn from, said chamber through means provided in one of said body members.

* * * * *